United States Patent [19]

Uldall et al.

[11] Patent Number: 5,106,368
[45] Date of Patent: Apr. 21, 1992

[54] COLLAPSIBLE LUMEN CATHETER FOR EXTRACORPOREAL TREATMENT

[75] Inventors: Peter R. Uldall, Willowdale, Canada; Michael P. DeBruyne, Bloomington, Ind.

[73] Assignee: Cook Incorporated, Bloomington, Ind.

[21] Appl. No.: 513,491

[22] Filed: Apr. 20, 1990

[51] Int. Cl.$^5$ .............................................. A61M 25/00
[52] U.S. Cl. ...................................... 604/43; 604/265; 604/178; 604/280; 604/4
[58] Field of Search ................... 604/43, 178, 265, 264, 604/280, 53, 27, 4

[56] References Cited

U.S. PATENT DOCUMENTS

| | | | |
|---|---|---|---|
| 883,583 | 3/1908 | Stallsmith | 604/43 |
| 1,696,018 | 12/1928 | Schellberg | 604/43 |
| 3,821,957 | 7/1974 | Riely et al. | 604/178 |
| 4,385,631 | 5/1983 | Uthmann | 604/43 X |
| 4,405,313 | 9/1983 | Sisley et al. | 604/43 |
| 4,406,656 | 9/1983 | Hattler et al. | 604/280 |
| 4,445,897 | 5/1984 | Ekbladh | 604/264 |
| 4,583,968 | 4/1986 | Mahurkar | 604/43 |
| 4,588,398 | 5/1986 | Daugherty et al. | 604/264 X |
| 4,623,327 | 11/1986 | Mahurkar | 604/4 |
| 4,626,240 | 12/1986 | Edelman | 604/280 X |
| 4,648,865 | 3/1987 | Aigner | 604/43 X |
| 4,681,564 | 7/1987 | Landreneau | 604/280 X |
| 4,738,666 | 4/1988 | Fuqua | 604/280 |
| 4,770,652 | 9/1988 | Mahurkar | 604/4 |
| 4,777,951 | 10/1988 | Cribier et al. | |
| 4,782,834 | 11/1988 | Maguire et al. | |
| 4,842,582 | 6/1989 | Mahurkar | 604/43 |
| 4,998,919 | 3/1991 | Pesch | 604/280 X |

FOREIGN PATENT DOCUMENTS 0168136 11/1986 European Pat. Off. .............. 604/43

OTHER PUBLICATIONS

McDowell et al., "A Simplified Technique for Percutaneous Insertion of Permanent Vascular Access Catheters in Patients Requiring Chronic Hemodialysis," *Journal of Vascular Surgery*, vol. 7, No. 4, Apr., 1988, pp. 574-576.
Denny et al., "Inferior Vena Cava: Translumbar Catheterization for Central Venous Access," *Radiology*, 1989, 170:1013-1014.
"Hickman Hemodialysis/Plasmapheresis Catheter," Bard Canada, Inc., Nov. 1989.

*Primary Examiner*—Edward M. Coven
*Assistant Examiner*—Sebastiano Passaniti
*Attorney, Agent, or Firm*—Richard J. Godlewski

[57] ABSTRACT

A dual lumen catheter is disclosed for providing extracorporeal treatment such as hemodialysis, which is percutaneously inserted for either short-term or long-term vascular access. The catheter includes a main body having proximal and distal segments connected to a pair of clamping limbs via a manifold. The distal segment includes two tubular members laterally attached to each other, one of which is thinner than the other and collapsible for inserting the catheter through a much smaller diameter peel-away sheath. Contrary to existing practices, the lengths of the arterial and venous tubular members are reversed such as to provide a longer negative pressure intake lumen. A hydrophilic slip coating covers the distal segment to further ease the insertion of the distal segment into the peel-away sheath. The cross-sectional area of the proximal segment is generally elliptical shaped for providing a leak proof fit through the vascular access site. A ring-like grommet moveable along the proximal segment anchors the catheter to the surrounding tissue. The lumens extending throughout the entire catheter are generally circular in nature and substantially equal in cross-sectional area to provide substantially equal flows of intake and return blood and to minimize clotting. The wall thickness of the negative pressure intake member is approximately one and a half to three times as thick as that of the thin-walled positive pressure tubular wall to maintain adequate flows of blood without collapsing or stretching.

20 Claims, 2 Drawing Sheets

COLLAPSIBLE LUMEN CATHETER FOR EXTRACORPOREAL TREATMENT

TECHNICAL FIELD

The present invention relates generally to extracorporeal treatments such as hemodialysis in which blood and its components are treated outside of the body and require access to the vascular system of the human body and, in particular, to multi-lumen catheters for use in such treatments.

BACKGROUND OF THE INVENTION

There is an increasing number of hemodialysis patients in whom creation and maintenance of an arteriovenous fistula is difficult or even impossible. For these patients, one prior art long-term catheter has provided a reasonable solution to their problems. It provides good blood flow and can be left in place in the external or internal jugular vein for many months or even years. The flow characteristics of this catheter are not ideal, but a plain tube catheter with an open end appears to maintain patency better than that of a tapered tube with side ports. The main problem with this plain tube catheter is its cross-sectional shape, which is similar to a double-barreled shotgun, and its' squared off ends. These features make it unsuitable for percutaneous insertion over a wire guide. As a result, this plain tube catheter has to be introduced with a cut-down surgical technique, which requires considerable time and skill.

A more serious problem with the plain tube catheter is that once it has been removed, it can not easily be reinserted into the same site. Therefore, jugular vein sites are soon used up and no longer available to the patient. One physician has used a peel-away sheath for percutaneous insertion of this catheter, but a very large 18 French sheath was required to accommodate the largest cross-sectional dimension of the catheter. Most physicians would judge the size of an 18 French introducer sheath to be undesirable.

Heretofore, it has always been considered necessary for the positive pressure return lumen to extend beyond the negative pressure intake lumen of a hemodialysis catheter. This is to ensure that blood returning from a hemodialysis treatment machine is delivered downstream from blood being extracted for purification. However, a problem with this configuration is that clots tend to adhere to the outside wall of the catheter at the entrance port to the shorter, negative pressure intake lumen.

To provide modern high efficiency dialysis, it is also desirable to utilize a catheter having two large diameter lumens for high blood flow rates and also having an external cross-sectional dimension which is not too large for vascular access. One such temporary access or short-term catheter includes a simple double-D lumen configuration. The walls of the catheter are thin, and the equal area lumens make full use of the available space. However, to insure that this catheter keeps its shape during high flow rate dialysis, the catheter is made of relatively stiff material which is unsuitable for long-term placement. If this temporary catheter is made of a silastic material, the intake lumen collapses under the influence of the strong negative intake pressure. Furthermore, the septum between the two lumens is pulled into the negative pressure lumen, thereby adversely changing the cross-sectional area in the two lumens as well as the blood flow rates therethrough.

Temporary or short-term catheters of the double-D configuration are used in large numbers all over the world, but they have a disconcerting tendency to get blocked. These catheters are made of a relatively stiff material to prevent the lumens from collapsing. A problem with the stiff material is that the catheter kinks or buckles when bent more than 180°. This also leads to lumen obstruction and the potential risk of cracking or splitting the wall. Furthermore, catheter stiffness combined with a tapered end for insertion over a guide wire has been responsible for many penetrating injuries of the wall of the superior vena cava or right atrium. There have been many deaths caused by such spontaneous perforations. This can occur by erosion, days or weeks after the catheter is originally inserted. However, no penetrating vein wall injuries have been reported with the use of blunt-end silastic catheters.

Silastic catheters with the double-barreled shot-gun configuration (two cylindrical lumens side by side) are remarkably resistant to kinking even when bent sharply through 180°. Also a cylindrical lumen is the theoretical optimum to achieve maximum flow for the smallest surface area of the wall. Finally, the cylindrical lumen avoids the sharp corners in the wall of the double-D configuration where, at least theoretically, clotting is more likely to occur.

The side-by-side open-ended design of the long-term catheter has much less tendency to block, but has not been used as a temporary catheter since it cannot easily be introduced percutaneously. The circular intake lumen of the long-term catheter is similarly recessed back from the distal end of the return lumen to minimize blood recirculation. A problem with this is that the wall of the extended positive pressure return lumen provides a surface for clots to adhere. In an attempt to solve this blockage problem, the walls of the negative pressure intake lumen are provided with side ports. However, it is believed that these side ports may actually encourage clotting.

The long term catheter typically employs a fixed-position dacron cuff which may not be conveniently positioned to stabilize the catheter. Removal of the catheter and release of the dacron cuff requires a new incision and dissection of the cuff by a surgeon. Dissecting the cuff from ingrown tissue invariably leads to bleeding, which may be hard to control.

SUMMARY OF THE INVENTION

The foregoing problems are solved and a technical advance is achieved with an illustrative extracorporeal treatment catheter having a collapsible lumen for percutaneous insertion into a blood vessel through a much smaller diameter peel-away introducer sheath. This extracorporeal treatment catheter comprises first and second elongated tubular members having respective first and second longitudinal passageways therein, commonly referred to as lumens. The first and second tubular members are laterally attached and have respective first and second walls with different thicknesses about the two lumens. Advantageously, the second lumen wall is thinner than the first lumen wall and is collapsible about the second tubular member for inserting them both into a blood vessel through a smaller diameter introducer sheath. When inserted in a vein, the collapsed lumen returns to its original shape. Preferably, the thickness of the first lumen wall is twice as thick as that of the second lumen wall. This advantageously permits percutaneous insertion of the catheter with a stiffening cannula over a wire guide and through the much smaller diameter introducer sheath. The distal end of the two tubular members includes a slippery-when-wet coating for further easing the percutaneous insertion of the catheter through the introducer sheath.

The intake lumen wall thickness is thick enough to withstand the negative pressure associated with hemodialysis treatment machines without the intake lumen collapsing. The return lumen wall is thinner than the intake lumen wall to allow it to collapse about the first member for percutaneous insertion through the smaller diameter introducer sheath, but yet thick enough to withstand the positive pressure of the returning blood without stretching. The thickness of the intake lumen wall to that of the return lumen wall may vary in a range of one and a half to three times as thick and still provide satisfactory blood flow characteristics. The cross-sectional shape of the two lumens are substantially equal in area to maintain balanced intake and return blood flows. Furthermore, the cross-sectional shape of the two lumens is generally circular to advantageously maintain maximum laminar blood flow for a given wall surface area.

As a departure in the art, the negative pressure intake lumen is longer than the positive pressure return lumen at the distal ends, which is opposite to that of presently available hemodialysis catheters. The shorter positive pressure return lumen advantageously reduces the accumulation of blood clots and resulting blockage with only a minimal increase in blood recirculation between the two lumens.

To eliminate the seepage of blood between the tubular members where they penetrate the vein wall, the catheter has been segregated into distal and proximal segments. For percutaneous insertion, the distal segment advantageously includes different thickness walls for collapsing the thin-walled positive pressure return lumen about the negative pressure intake lumen and inserting the collapsed distal segment through a smaller diameter introducer sheath. Extending proximally from the distal segment, the proximal segment has a cross-sectional shape of a generally elliptical character to form a leak proof fit when inserted into the vein wall. Furthermore, both of the segments are formed from a biocompatible material such as silastic for long-term use and have a predetermined durometer for pushing the catheter through the introducer sheath and blood vessel.

The catheter also advantageously includes a moveable collar or grommet which can be adjusted in position on the proximal segment and has a flange extending therefrom to secure the catheter to the surrounding tissues. The grommet can be released by simply pulling on it or by dissecting it out. In either case, there is no bleeding.

DETAILED DESCRIPTION

Figure 1:
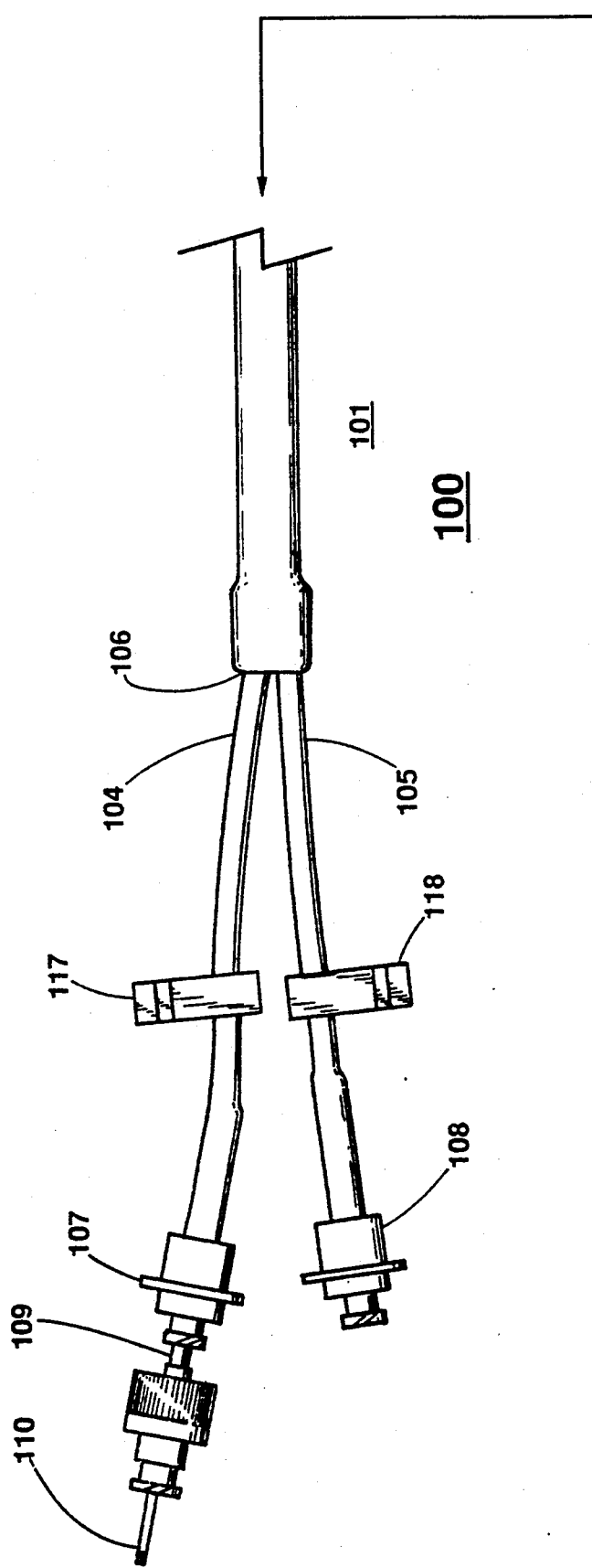
FIG. 1 depicts a dual lumen hemodialysis catheter having a collapsible lumen for percutaneous insertion through a peel-away introducer sheath of the present invention.
Figure 1:
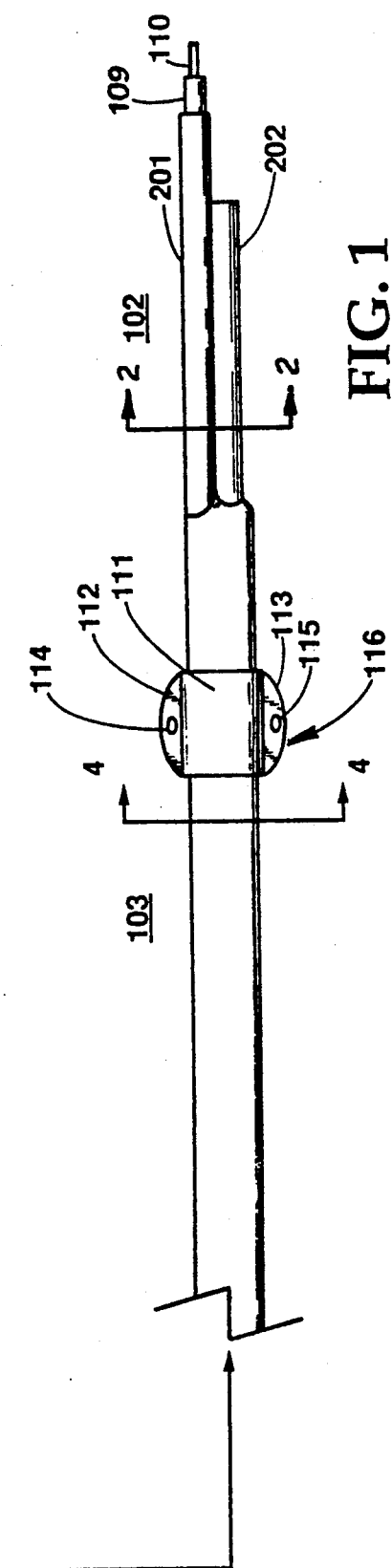

Depicted in FIG. 1 is a dual lumen catheter 100 for use in an extracorporeal treatment such as hemodialysis and the like. This vascular access catheter is percutaneously inserted in a blood vessel, such as preferably the jugular or femoral vein, for either short-term or long-term hemodialysis treatment of the patient. The jugular access site is preferable to the subclavian vein because it is much less likely to cause subclavian vein thrombosis. Subclavian vein thrombosis is a serious long-term disability for a patient on dialysis if it is not diagnosed and successfully treated at an early stage, because it interferes with A-V fistula construction in the ipsilateral arm, leading to a permanently swollen congested arm as long as the fistula is functioning. Internal jugular vein thrombosis is probably not common after internal jugular cannulation, but it causes no disability even if it occurs and is not treated, except that the patient loses a potential access site.

The catheter basically comprises a dual lumen main body 101 attached to a single lumen, arterial clamping limb 104 and a single lumen, venous clamping limb 105 via interconnecting manifold 106. For connection to extracorporeal treatment equipment, two female Luer lock connectors 107 and 108 are connected in a well-known manner to arterial and venous clamping limbs 104 and 105, respectively. The main body of the catheter includes a distal segment 102 and a proximal segment 103 extending proximally therefrom and is comprised of a flexible biocompatible material such as 70 durometer silicon or silastic. Distal segment 102 includes a thick-walled, negative pressure, elongated tubular member 201 and a shorter, thin-walled, collapsible, positive pressure, elongated tubular member 202 attached laterally thereto. The catheter further includes lockable clamps 117 and 118 for clamping arterial and venous clamping limbs 104 and 105, respectively. One such clamp is the BETA-CAP clamp available from Quinton Instrument Co., Seattle, Washington. Slide clamps from the Qosina Co. are also acceptable.

Catheter 100 also includes an anchoring grommet 116 having a ring-like collar 111 positioned around and slidably moveable along proximal segment 103. Flange 112 and 113 extend laterally from the collar and have respective apertures 114 and 115 formed therein to insert sutures therethrough. The grommet is positioned on the proximal segment where it crosses the supraclavicular fossa. Sutures placed through the apertures secure the catheter to the surrounding tissue. The shape of the grommet permits capture of the catheter without compressing it. The smooth rounded flanges allow the grommet to be pulled out with the catheter when it is removed. The anchoring sutures will tear out of the flanges and the only thing left inside the patient will be the sutures themselves.

The overall length of the main body of the catheter from the manifold to the distal tip thereof depends on the insertion site selected by the physician. When inserted in the right jugular vein, the main body of the catheter from manifold to tip is preferably 26 cm in length with an 11 cm distal segment. For the left jugular site, the main body of the catheter is approximately 30 cm in length with the distal segment being 15 cm. As suggested, the distal segment 102 includes a collapsible tubular member 202 for inserting the distal segment with stiffening cannula 109 inserted in tubular member 201 over wire guide 110 through a well-known smaller diameter peel-away introducer sheath (not shown). The introducer sheath which should be no more than 10 cm in length. This will allow the distal segment to be inserted into the sheath with the distal tip protruding slightly beyond the distal end of the sheath before it is peeled away.

Figure 2:
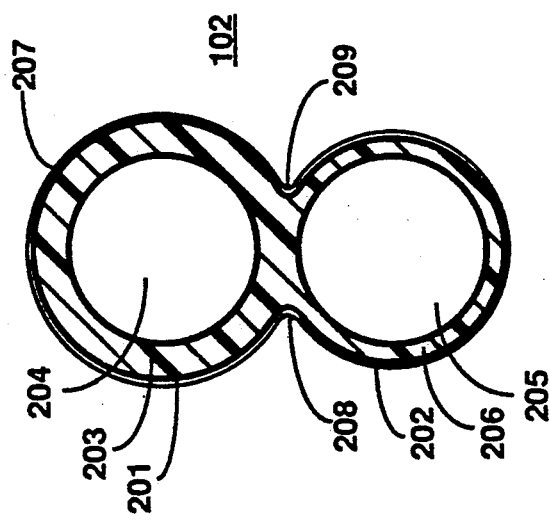
FIG. 2 depicts a cross-sectional view of the distal segment of the catheter of FIG. 1 along the line 2—2.

Depicted in FIG. 2 is a cross-sectional view of distal segment 102 along the line 2—2 of FIG. 1. Distal segment 102 includes thick-walled elongated tubular member 201 and thin-walled elongated tubular member 202 attached laterally to member 202 and collapsible thereon. The thick-walled tubular member includes first wall 203 surrounding first longitudinal passageway 204 included therein. This first longitudinal passageway is designated a negative pressure intake lumen for receiving blood from the vessel of a patient for hemodialysis treatment. By way of example, the thickness of first wall 203 is approximately 0.020" with the cross-sectional diameter of passageway 204 being approximately 0.080". The distal end of the negative pressure intake lumen may be outwardly tapered to prevent clotting and the collection of blood clots thereon. The dimensions of tubular member 201 and negative pressure lumen 204 allow for blood flow rates of 350–400 ml per minute without collapsing.

The second, thin-walled collapsible tubular member 202 includes a second longitudinal passageway 205 with second wall 206 positioned thereabout. The thickness of second wall 206 is approximately 0.010" with longitudinal passageway having a cross-sectional diameter of approximately 0.080", which is equivalent to that of passageway 204. In an uncollapsed state, the maximum cross-sectional dimension of distal segment is approximately 0.210" plus allowances for fabrication and slip coating 207, which will pass through an 18 French (0.236") aperture. Second longitudinal passageway 205 is designated the positive pressure return lumen for returning blood from a hemodialysis machine to the vessel of the patient. The cross-sectional area of passageways 204 and 205 are substantially equivalent to provide approximately equal flow rates to and from the patient. The distal segment also includes slip coating 207 which acts as a lubricant to insert the distal segment through the introducer sheath. One such slip coating is a slippery-when-wet hydrophilic coating that is commercially available from Hydromer Inco., Whitehouse, N.J. The slip coating is applied to the outside surface of distal segment 102. This hydrophilic slip coating is wetted during the insertion procedure to provide a slippery surface for easier insertion through the peel-away introducer sheath. Furthermore, the presence of blood or other fluids in the introducer sheath further lubricates the collapsed distal segment as it is being inserted therethrough. This further eases the percutaneous insertion of the catheter when inserting a collapsed catheter having an 18 French uncollapsed cross-sectional dimension through a 12 French introducer sheath. Another lubricious slip coating is Dow Corning medical-grade silicone fluid spray (a non-allergenic silicone lubricant) which is commercially available from Dow Corning Europe, Inc., Health Care Group, Brussels, Belgium. This silicone spray is applied to the distal segment by the physician just prior to percutaneous insertion of the catheter.

Experimentally, a 30 cm thin-walled, positive pressure member of a 70 durometer silicon material catheter was able to tolerate a blood flow of 500 ml per minute and a negative pressure of 300 mm/Hg without collapsing when flows were reversed, and it was used as a negative pressure lumen. In clinical practice, the ability to reverse the flows is important if on occasion the thick-walled lumen fails to provide adequate out flow. The dialysis treatment community has been demanding these flow rates, but until now has not been provided with catheters to provide these flow rates. Experiments indicate that blood flow rates of 400 ml per minute are attainable with arterial and venous pressure barely exceeding 200 mm of mercury.

The cross-sectional shape of the passageways are also preferably circular to maintain laminar fluid flow. The introduction of a smaller radius into the cross-sectional shape of the passageway typically provides opportunities for the blood flow to become turbulent and increases the risk of clotting.

A number of competing factors are involved with the dimensions associated with the wall thicknesses and lumen diameters. The tubular members must be thin and flexible enough for insertion into the vascular system without kinking or collapsing in operation. Negative pressure lumen wall 203 must be thick enough to withstand the negative pressures inwardly exerted thereon by modern hemodialysis treatment machines without collapsing during intake of blood from the patient. Thinner, positive pressure lumen wall 206 must be thick enough to withstand the positive pressures outwardly exerted thereon without stretching. The diameter of the passageways should be as large as possible to provide adequate flow rates as demanded by the hemodialysis treatment community. Lastly, the maximum cross-sectional dimension of the catheter must be minimal for percutaneous insertion into the blood vessel such as through a 12 French (0.158") peel-away introducer sheath. As a result, the thickness of negative pressure lumen wall 203 is preferably twice as thick as that of positive pressure lumen wall 206. Furthermore, the thickness of negative pressure lumen wall 203 may range from one and a half to three times as thick as that of positive pressure lumen wall 202.

Figure 3:
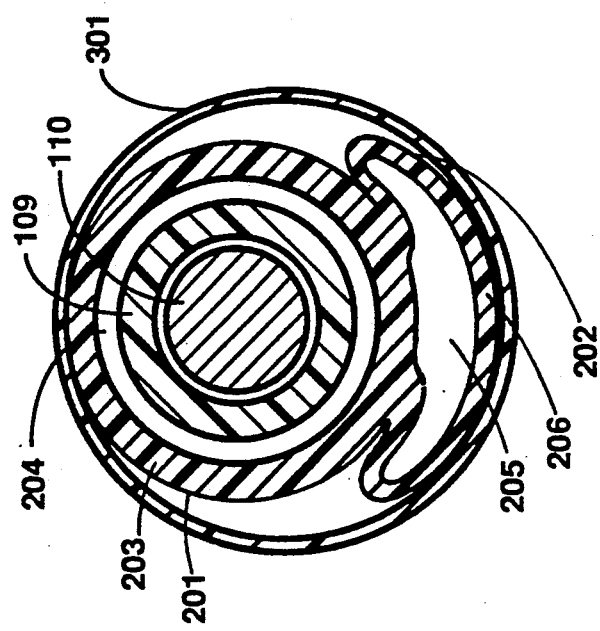
FIG. 3 depicts a cross-sectional view of the distal segment of the catheter of FIG. 1 in a collapsed state and positioned in an introducer sheath.

This thin wall construction permits the collapse of tubular member 202 including positive pressure lumen 205 and wall 206 about tubular member 201 as depicted in FIG. 3. In the collapsed state, a hemodialysis catheter typically having a maximum cross-sectional dimension of 18 French can be percutaneously inserted with stiffening cannula 109 over wire guide 110 into a blood vessel through a much smaller 12 French diameter peel-away introducer sheath 301.

Figure 4:
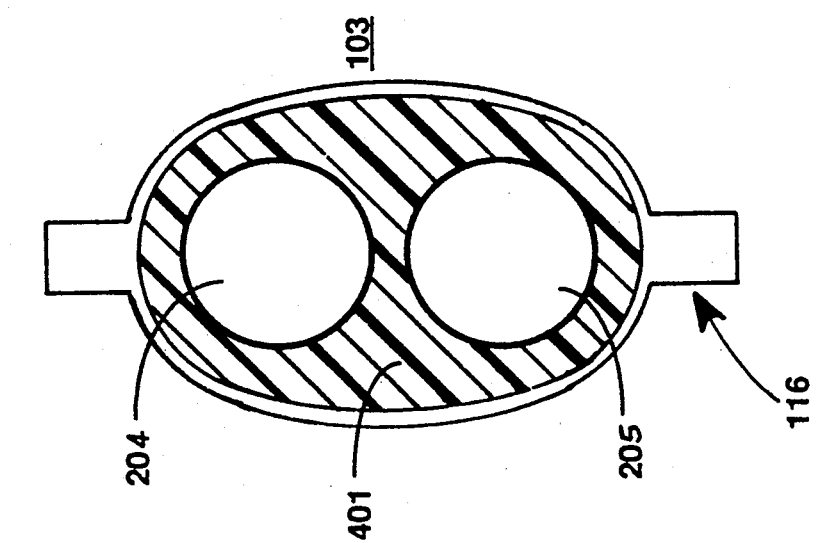
FIG. 4 depicts a cross-sectional view of the proximal segment of the catheter of FIG. 1 along the line 4—4.

Depicted in FIG. 4 is a cross-sectional view of proximal segment 103 along the line 4—4 of FIG. 1. The cross-sectional shape 401 of the proximal segment is formed to provide a tight fit between the main catheter body and the vascular access insertion site. Preferably, the cross-sectional shape is elliptical to prevent the seepage of blood from the vascular access site along the outside surface of the proximal segment of the main catheter body. Respective negative and positive pressure lumens 204 and 205 extend entirely through proximal segment 103.

To insert the dual lumen catheter using the well-known Seldinger technique, a wire guide 110 is inserted through an introducer needle into the accessed vein. The introducer needle is removed, and a 12 French sheath mounted on a dilator is directly inserted over the guidewire into the vein. Stiffening cannula 109 is inserted through the negative pressure lumen of the arterial clamping limb 104, proximal segment 103, and out the distal tip end of distal segment 102. The catheter and stiffening cannula are inserted over wire guide 110 and through the peel-away sheath with the thin-walled tubular member 202 collapsed. The peel-away sheath is removed after the distal segment is inserted through the sheath into the vein. A short distal portion of the elliptically shaped proximal segment 103 is then inserted through the venous access site into the vein, thereby establishing a relatively tight and leak-proof seal.

Grommet 116 is mounted onto the catheter by passing it over the distal tip, after the catheter has been pulled up through the subcutaneous tunnel and before the catheter is inserted through the sheath into the vein. Grommet 116 slides the distal segment and a length of proximal segment 103 and is placed strategically in the supraclavicular fossa and anchored to the subcutaneous tissue before the supraclavicular wound is closed. Final position of the grommet will vary in each patient according to how much length of the catheter is desired in the blood vessel.

To change the catheter, it will only be necessary to reopen the supraclavicular incision and remove the subcutaneous silk sutures which are anchoring the grommet in place. To remove the catheter without intending to replace it with another one in that same track, the catheter is subjected to a steady pull. This will tear the sutures out of the flanges of the grommet.

Of course, it will be understood that the afore-mentioned dual lumen extracorporeal treatment catheter is merely illustrative of the application of the principles of this invention and that numerous other arrangements may be devised by those skilled in the art without departing from the spirit and scope of the invention. In particular, a number of other grommets may be slid over or attached to the proximal segment of the catheter for anchoring the catheter to surrounding tissue. The catheter may also include any number of other connectors or clamping devices for use with the arterial and venous clamping limbs. Furthermore, the shape of the lumens may be varied to an elliptical or even crescent shape; however, the radii of lumen shapes need to be maximized to prevent or minimize turbulent blood flow and the possibility of clotting.

What is claimed is:

1. A hemodialysis catheter for extracorporeal treatment, comprising:
    a first elongated member having a first, negative pressure intake lumen extending longitudinally therein and a first wall positioned about and defining said first lumen, said first lumen having a first predetermined cross-sectional area, said first wall having a first predetermined thickness for maintaining said first area when a predetermined negative pressure is applied to said first lumen; and
    a second elongated member attached to said first member and having a second, positive pressure return lumen extending longitudinally therein and a second wall having a second predetermined thickness positioned about and defining said second lumen and collapsible on said first wall for insertion through a narrower introducer sheath and into a blood vessel, said second lumen having a second predetermined cross-sectional area, said second wall returning to and maintaining said second area when introduced into said blood vessel.

2. The catheter of claim 1 wherein said first wall thickness is approximately two times as great as said second wall thickness.

3. The catheter of claim 1 wherein said first wall thickness is at least one and a half times as thick as said second wall thickness.

4. The catheter of claim 1 wherein said first wall thickness is in a range of one and a half to three times as thick as said second wall thickness.

5. The catheter of claim 1 wherein said first and second cross-sectional areas are generally circular.

6. The catheter of claim 1 wherein said first and second cross-sectional areas are approximately equal.

7. The catheter of claim 1 wherein said first and second members have respective first and second predetermined lengths, said first member being longer than said second member at distal ends thereof.

8. The catheter of claim 1 further comprising a slip coating about a distal end of said first and second members.

9. A hemodialysis catheter for extracorporeal treatment comprising:
    a first elongated segment having first, negative pressure intake lumen and second, positive pressure return lumen extending longitudinally therein and first and second walls, said first wall positioned about and defining said first lumen, said first lumen having a first predetermined cross-sectional area, said first wall having a first predetermined thickness for maintaining said first area when a predetermined negative pressure is applied to said lumen, said second wall positioned about and defining said second lumen, said second lumen having a second predetermined cross-sectional area, said second wall attached to said first wall and having a second predetermined thickness, said second lumen being collapsible on said first wall, said second wall returning to and maintaining said second area when said first segment is introduced into a blood vessel; and
    a second elongated segment extending proximally from said first segment having said first and second longitudinal passageways extending therein.

10. The catheter of claim 9 wherein said second elongated segment has a predetermined cross-sectional shape.

11. The catheter of claim 10 wherein said predetermined shape is generally elliptical.

12. The catheter of claim 9 further comprising a collar positionable about said second segment and having a flange securable to tissue.

13. The catheter of claim 9 wherein said first wall thickness is at least one and a half times as thick as said second wall thickness.

14. The catheter of claim 9 wherein said first wall thickness is less than three times as thick as said second wall thickness.

15. The catheter of claim 9 wherein said first elongated segment includes a slip coating.

16. The catheter of claim 9 wherein said first lumen has a first predtremined length and said second lumen has a second predetermined length, said first lumen being longer than said second lumen at a distal end of said first segment.

17. The catheter of claim 9 wherein said first and second segments comprise a biocompatible material having a predetermined durometer.

18. The homodialysis catheter of claim 9 wherein said first and second cross-sectional areas are generally circular.

19. The catheter of claim 9 wherein said first and second cross-sectional areas are approximately equal.

20. A collapsible dual-lumen hemodialysis catheter for percutaneous insertion through a narrower introducer sheath, comprising:

an elongated distal segment having a negative pressure intake lumen and a positive pressure return lumen extending longitudinally therein, said lumens having substantially equivalent cross-sectional circular areas and first and second walls, said first wall positioned about and defining said intake lumen and having a first predetermined thickness for maintaining said cross-sectional circular area of said intake lumen when a predetermined negative pressure is applied to said intake lumen, said second wall positioned about and defining said return lumen and having a second predetermined thickness, said first thickness being approximately twice as thick as said second thickness, said first wall being a predetermined distance longer than said second wall at a distal end of said distal segment, said distal segment in a collapsed state having said second wall and said return lumen being collapsed on said first wall and having a maximum cross-sectional dimension less than said narrower introducer sheath for insertion through said sheath in a blood vessel, said second wall returning to and maintaining said cross-sectional circular area of said return lumen when said distal segment is introduced into said blood vessel, said distal segment also having a slip coating thereon;

an elongated proximal segment extending proximally from said distal segment and having a generally elliptical cross-sectional shape, said lumens extending longitudinally through said proximal segment; and a moveable collar positioned about said proximal segment and having a flange with a suture hole therein.

* * * * *